(12) United States Patent
Ranieri et al.

(10) Patent No.: US 7,678,575 B2
(45) Date of Patent: Mar. 16, 2010

(54) METHOD FOR THE DETECTION OF PHOSPHINE IN CEREALS

(75) Inventors: Roberto Ranieri, Parma (IT); Marco Silvestri, Parma (IT); Angelo Visconti, Bari (IT); Michelangelo Pascale, Bari (IT); Francesco Longobardi, Acquaviva delle Fonti (IT)

(73) Assignees: Barilla G.e R. Fratelli S.p.A. (IT); Consiglio Nazionale delle Ricerche (IT)

( * ) Notice: Subject to any disclaimer, the term of this patent is extended or adjusted under 35 U.S.C. 154(b) by 244 days.

(21) Appl. No.: 11/829,302

(22) Filed: Jul. 27, 2007

(65) Prior Publication Data

US 2008/0026469 A1 Jan. 31, 2008

(30) Foreign Application Priority Data

Jul. 28, 2006 (EP) .................................. 06425533

(51) Int. Cl.
*G01N 33/02* (2006.01)
(52) U.S. Cl. .................... 436/20; 436/166; 436/172; 422/82.09; 422/86; 422/102
(58) Field of Classification Search .................... 436/20, 436/166, 172; 422/82.09, 86, 102

See application file for complete search history.

(56) References Cited

U.S. PATENT DOCUMENTS 4,933,529 A 6/1990 Saville

FOREIGN PATENT DOCUMENTS

GB 2 381 581 5/2003

OTHER PUBLICATIONS

Nowicki, T.W., "Gas-Liquid Chromatography and Flame Photometric Detection of Phosphine in Wheat," J. Assoc. Off. Anal. Chem., 61:4,829-836 (1978).*
Rangaswamy, J.R., "Simple Spectrophotometric Method for Determination of Phosphine Residues in Wheat," J. Assoc. Off. Anal. Chem., 67:1, 117-122 (1984).*
Ren, Y-L, et al., "Realease of Fumigant Residues from Grain by Microwave Irradiation," Journal of AOAC International, 81:3, 673-678 (1998).

(Continued)

*Primary Examiner*—Lyle A Alexander
*Assistant Examiner*—Dwan A Gerido
(74) *Attorney, Agent, or Firm*—Akerman Senterfitt

(57) ABSTRACT

A method is described for the total phosphine detection in cereal caryopses, comprising the steps of inserting a sample of cereal caryopses inside a container (1) equipped with hermetic closure (2); adding to the sample an aqueous solution of $H_2SO_4$ with a v/v concentration in the range of 5-20%, with obtainment of an aqueous dispersion, and hermetically clos-

A　　　　B　　　　C ing the first container (1); subjecting the aqueous dispersion contained in the first container (1) to the action of microwaves for a time not greater than 3 minutes; drawing a predetermined volume of gas overlying the aqueous dispersion and detecting the phosphine possibly present by means of colorimetric and/or spectrophotometric methods, preferably by bringing it into contact with a predetermined volume of an aqueous solution of $AgNO_3$ of known molarity, inside a second container (3) with hermetic closure and visually analysing the obtained color and/or spectrophotometrically measuring the absorbance at 400 nm of the aqueous solution. Equipment for the execution of the aforesaid method is described.

13 Claims, 2 Drawing Sheets

OTHER PUBLICATIONS

Bruce, R.B., et al., "Phosphine Residues from Phostoxin-Treated Grain," Agricultural and Food Chemistry, 10:1, 18-21 (1962).

Nowicki, T.W., "Gas-Liquid Chromatography and Flame Photometric Detection of Phosphine in Wheat," J. Assoc. Off. Anal. Chem., 61:4, 829-836 (1978).

Allen, S.E., et al., "Comparison of Six Methods for Determining Aged Phosphine Residues in Wheat," Journal of AOAC International, 81:3, 633-637 (1998).

Rangaswamy, J.R., "Spectrophotometric Method for Determination of Phosphine Residues in Cashew Kernels," J. Assoc. Off. Anal. Chem., 71:3 557-559 (1988).

Townshend, A., "Sample Dissolution for Elemental Analysis," Encyclopedia of Analytical Science, 8: 4510-4518 (1995).

\* cited by examiner

METHOD FOR THE DETECTION OF PHOSPHINE IN CEREALS

FIELD OF APPLICATION

The present invention refers in general to the agrifood industry sector.

In particular, the invention regards a rapid method for the detection of phosphine in cereals.

PRIOR ART

Phosphine ($PH_3$) is a gas used to protect the cereals stored in silos from insect attack. Phosphine is generated by fumigation inside the silos, using aluminium and/or magnesium phosphide tablets which release the phosphine in contact with the air and humidity.

Phosphine is very effective in the protection of the cereal caryopses from insects and other infesting agents but is also characterised by a non-negligible toxicity. It decomposes in the air after about 24 hours and at high concentrations spontaneously combusts, freeing the toxic vapours of $P_2O_3$ and $P_2O_5$. The threshold limit for a work day (the so-called TLV-TWA "Threshold Limit Value-Time Weighted Average") is equal to 0.3 ppm (v/v); in general, a concentration in air greater than 8 ppm normally causes vomiting and nausea while exceeding the threshold of 200 ppm can be lethal.

As reported in the Codex Alimentarius of FAO/WHO, Vol. 2, *Pesticide residues in food*, the maximum residue limit (MRL, Minimum Residue Level) established for the cereal caryopses is 0.1 µg of phosphine per g of matrix (ppm, m/m). The limit is referred to the total phosphine obtained by the sum of the gaseous phosphine physically absorbed on the matrix and that deriving from all the phosphides present (D. M. Jan. 22, 1998 concerning maximum limits of the residues of active substances of the phytosanitary products tolerated in the products intended as food).

It is known that Rangaswamy J. R., J Assoc. Off. Anal. Chem., 1984, 67(1): 117-22, a spectrophotometric method for the detection of the phosphine in wheat samples, whose phosphine is extracted by soaking the wheat with a solution of $AgNO_3$ for 1 hour. After filtration and centrifugation, the absorbance of the extract is measured at 400 nm. The total analysis time is about 1 hour.

Nowicki T. W. (Gas-liquid chromatography and flame photometric detection of phosphine in wheat. *J. Assoc. Off. Anal. Chem.* (1978), 61(4): 829-836) has described a method for the detection of the phosphine in grain, which comprises the treatment of a grain sample with a 10% $H_2SO_4$ solution heated under reflux conditions; in such a manner all of the phosphine is liberated from the wheat and it is measured by analysing the developed gas by means of gas-chromatography. In fact, in the headspace (gas overlying the solution), in addition to the absorbed phosphine, phosphine is also liberated which derives from the acidic hydrolysis of the phosphides possibly present in the sample to be analysed. The total analysis time is about 40 minutes.

A method is noted which uses microwaves to liberate the phosphine absorbed by wheat samples contained in sealed containers (Ren Y. L. and Desmarchelier J. M., Release of fumigant residues from grain by microwave irradiation), *Journal of the Association of Official Analytical Chemists International* (1998), 81(3), 673-678), and foresees the subsequent gas-chromatography detection of the phosphine contained in the gaseous phase present in the headspace of the containers. The total analysis time is about 5 minutes.

SUMMARY OF THE INVENTION

The problem underlying the present invention was that of making available a method for the detection of the total phosphine in cereal samples which has an accuracy and precision comparable to the abovementioned known spectrophotometric method and at the same time permits considerably reducing the times required for analysis.

A similar problem has been resolved, according to the invention, by a method for the detection of the total phosphine in cereal caryopses comprising the steps of:

a) inserting a sample of said cereal caryopses inside a container equipped with hermetic closure;

b) adding to said sample an aqueous solution of $H_2SO_4$ with a v/v concentration in the range of 5-20%, with obtainment of an aqueous dispersion, and hermetically closing said container;

c) subjecting the aqueous dispersion contained in the container to the action of microwaves for a time not greater than 3 minutes;

d) drawing a predetermined volume of gas overlying the aqueous dispersion and detecting the phosphine possibly present in this by means of calorimetric and/or spectrophotometric methods.

According to a preferred embodiment, the aforesaid predetermined volume of gas is brought into contact with a predetermined volume of $AgNo_3$ aqueous solution of known molarity, inside a further container with hermetic closure, and after stirring the absorbance of said aqueous solution at 400 nm is spectrophotometrically measured. Alternatively, it is possible to carry out a semi-quantitative detection, by means of a visual analysis of the yellow-brown colour developed in the second container following the reaction between phosphine and $AgNo_3$.

The concentration of the $AgNo_3$ solution is preferably in the range of $0.1\text{-}1.8 \times 10^{-4}$ M. According to an alternative realisation mode, the detection of the phosphine as stated in step d) is carried out by placing the aforesaid predetermined gas volume in contact with a paper medium soaked with a reagent capable of developing a colouration by reaction with the phosphine and chosen from the group comprising $AgNO_3$, $HgCl_2$, mixtures of $AgNO_3$ and $HgCl_2$ and a mixture of dimethyl yellow, cresol red, and $HgCl_2$. The concentration of the aqueous solution of sulphuric acid is preferably about 8-12% v/v. The microwaves used preferably have a power in the range of 80-200 W, conveniently about 100-140 W, and the exposure time to the microwaves is preferably in the range of 90-150 seconds. With the method according to the present invention, the advantage is attained of being able to detect, in a very rapid manner (analysis time not greater than 3 minutes), the total phosphine (i.e. the phosphine absorbed and that deriving from the possibly present phosphides) contained in a sample of cereal caryopses, due to the combined action of the sulphuric acid and the microwaves.

The method according to the present invention can be carried out with equipment which comprises: a first container intended to contain an aqueous dispersion of a sample of cereal caryopses and an aqueous solution of sulphuric acid and equipped with hermetic closure means; means for subjecting the aqueous dispersion contained in the first container to the action of microwaves; means for transferring a predetermined aliquot of the gaseous phase overlying the aforesaid aqueous dispersion, developed following the application of the microwaves, to a second container containing an aqueous solution of $AgNO_3$, it too equipped with hermetic closure means; and means for the detection of the absorbance at 400 nm of the solution contained in the second container.

The first container can consist of a small bottle with a cap equipped with a puncturable Teflon® baffle and means for transferring the gaseous phase can consist of a syringe for gas. The second container can consist of a glass vial equipped with a cap with puncturable Teflon® baffle.

Alternatively, the second container can consist of a vacuum tube equipped with a cap with Teflon® baffle already containing the $AgNO_3$ vacuum solution. In this case, the transfer of the aliquot of gaseous phase from the first to the second container will occur by means of the use of a gastight device composed of two needles connected with each other by a flexible tube equipped with valve. In particular, one needle is inserted in the first container and the other in the second by keeping the valve initially in closed position. Following the opening of the valve, part of the headspace of the first container flows into the second container due to the vacuum.

At the same time as the aforesaid spectrophotometric method, it is possible to carry out the semi-quantitative detection of phosphine in cereal caryopses by means of a visual analysis of the yellow-brown colour of the solution (contained in the second container), which developed following the reaction between phosphine and $AgNO_3$.

DETAILED DESCRIPTION OF THE INVENTION

The present invention will be further described by making reference to the aforesaid figures and to several embodiments reported here below as illustrative and not limiting.

Figure 1:
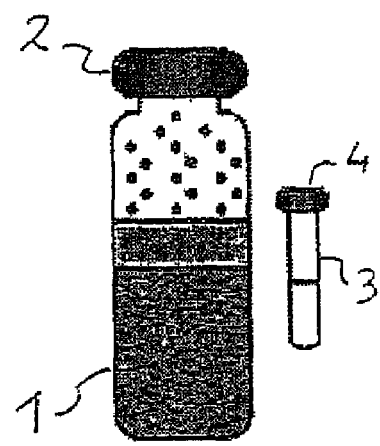
In FIG. 1, two containers used in the method according to the present invention are schematically represented.

Equipment is used comprising a first container 1 (FIG. 1), composed of a small bottle, intended to contain an aqueous dispersion of a sample of cereal caryopses and an aqueous solution of sulphuric acid and equipped with a hermetic closure cap 2 bearing a puncturable Teflon® baffle, and a second container 3, composed of a vial containing an aqueous solution of $AgNO_3$, it too equipped with a hermetic closure cap 4 with puncturable Teflon® baffle.

Using the abovementioned equipment, 20 g of a sample of hard wheat caryopses were inserted in a small glass bottle 1 of 60 ml volume and to this an additional 20 ml of an aqueous 10% $H_2SO_4$ solution was added. The small bottle was closed with a cap equipped with a puncturable Teflon® baffle and was inserted in a microwave oven. Microwaves were applied with a power of 120 W for 2 minutes, after which it was left to cool for 1 minute at room temperature and was stirred for 3 minutes to favour the $PH_3$'s complete passage into the gaseous phase.

Subsequently, 5 ml of gas produced in the headspace of the small bottle 1 was drawn with a gas syringe; this gas aliquot was injected into the glass vial 3 (4 ml volume) containing 1 ml of $(1.8 \times 10^{-4}$ M) $AgNo_3$ aqueous solution through the puncturable baffle of the cap 4. It is stirred on vortex for 1 minute and the cap 4 is opened, obtaining, in the presence of phosphine, the formation of a yellow-brown chromophore with absorption maximum at 400 nm.

The solution contained in the vial 3 was analysed by means of visual analysis of the colour and/or transferred into a spectrophotometer cuvette and the absorption was measured (after 1 minute from the opening of the cap 4).

Alternatively, it is possible to carry out the drawing of a specific gas volume (for example 10 ml) produced in the headspace of the small bottle 1 by means of a gas syringe at whose interior a disc of filter paper is housed, soaked in a solution of 0.1 M $AgNo_3$. In the presence of phosphine, the paper after 1 minute takes on a yellow-brown colour, permitting the distinction between uncontaminated samples and samples contaminated with phosphine at levels around or greater than the legal limit (0.1 µg/g).

To evaluate the recovery values related to the extraction step, samples were analysed contaminated with known quantities of $PH_3$, in triplicate, at three different levels (0.05, 0.10 and 0.25 µg/g). The samples were subjected to extraction with microwaves following the above described method. After cooling and stirring, 100 µl of headspace was analysed by means of a gas-chromatography reference method which uses the nitrogen-phosphorus detector (NPD). The results obtained by the GC analysis have shown an average recovery close to 100% (98-99%) with a variability of $\leq 10\%$.

Figure 2:
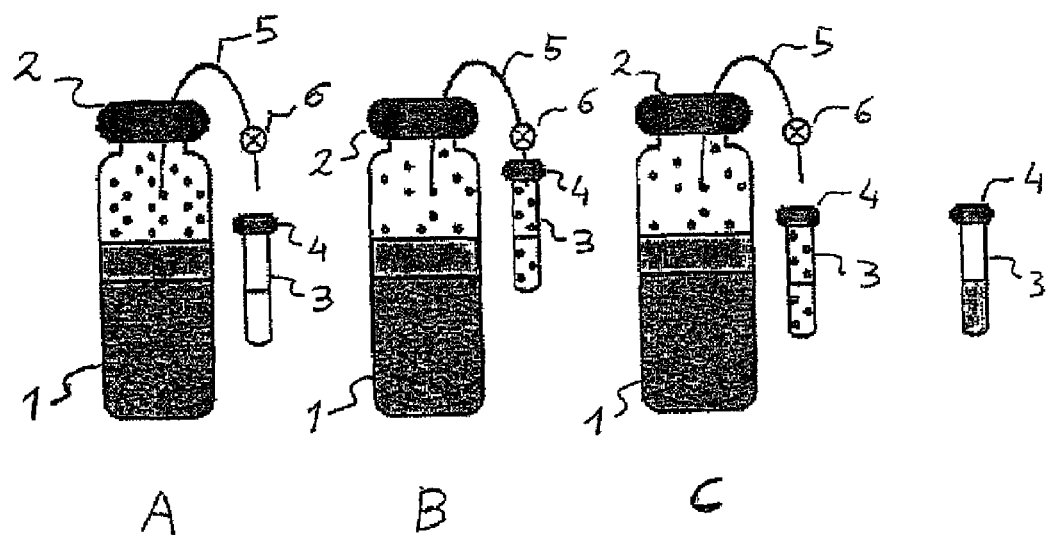
In FIG. 2, a realisation mode of equipment for the execution of the method according to the present invention is schematically represented.

Detections were carried out of the phosphine level contained in wheat samples, in particular hard wheat, according to the present method and using the above described equipment as alternative equipment, involving the use of vacuum tubes 4 and a gastight device 5, equipped with valve 6 and comprising two needles connected with each other by a small flexible tube. In this case, with reference to FIG. 2, in a first step A the phosphine possibly developed following the microwave treatment of the dispersion of cereal caryopses and sulphuric acid is found in the gaseous phase in the upper part of the container 1. In the Teflon® baffle of the cap 2, a needle of the device 5 is inserted, equipped with valve 6 in closed position while a solution of $AgNo_3$ of known molarity is contained vacuum-sealed in the container 3.

In step B, the free end of the device 5 is inserted inside the container 3, through the Teflon® baffle of the cap 4 and the valve 6 is opened, allowing the flow into the container 3 of a specific volume of the gas which is found in the upper part of the container 1.

In step C, the device 5 is extracted from the baffle of the cap 4 of the container 3, which is then stirred and analysed visually and/or at the spectrophotometer.

Regarding the results obtained in the detection of the phosphine level in the analysed samples, the following is observed.

Figure 3:
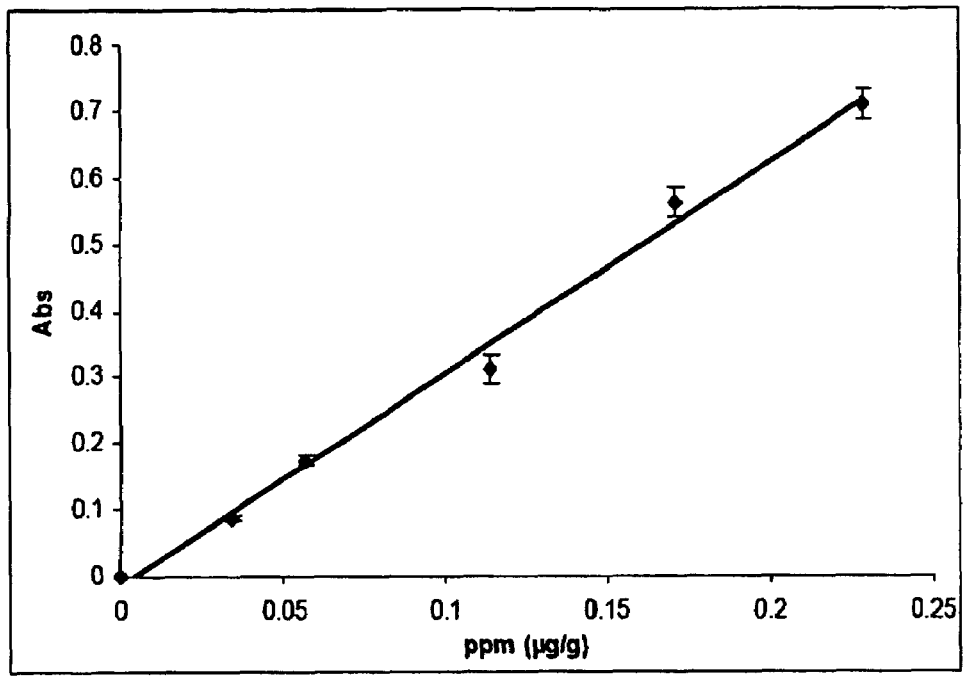
FIG. 3 is a graph showing a calibration line obtained by diluting a contaminated wheat sample with uncontaminated wheat.

The calibration line in matrix reported in FIG. 3, obtained by diluting a contaminated wheat sample with uncontaminated wheat, shows that a good linear response ($R^2=0.9930$) is obtained in the analysed concentration range (0.03-0.230 µg/g), with variation coefficients less than 7% (number of repetitions less than 3). The detection limit of the method was equal to 0.026 µg/g in matrix, well below the maximum admissible limit fixed by the European Community (0.1 µg/g).

From the visual comparison of the colour of the solutions contained in the container 3 after the reaction with the gas produced in the container 1 (see FIG. 1), it was possible to discriminate between wheat samples which have not been contaminated by contaminated samples and wheat samples at different levels of phosphine contamination (0.060, 0.120 and 0.230 µg/g).

Figure 4:
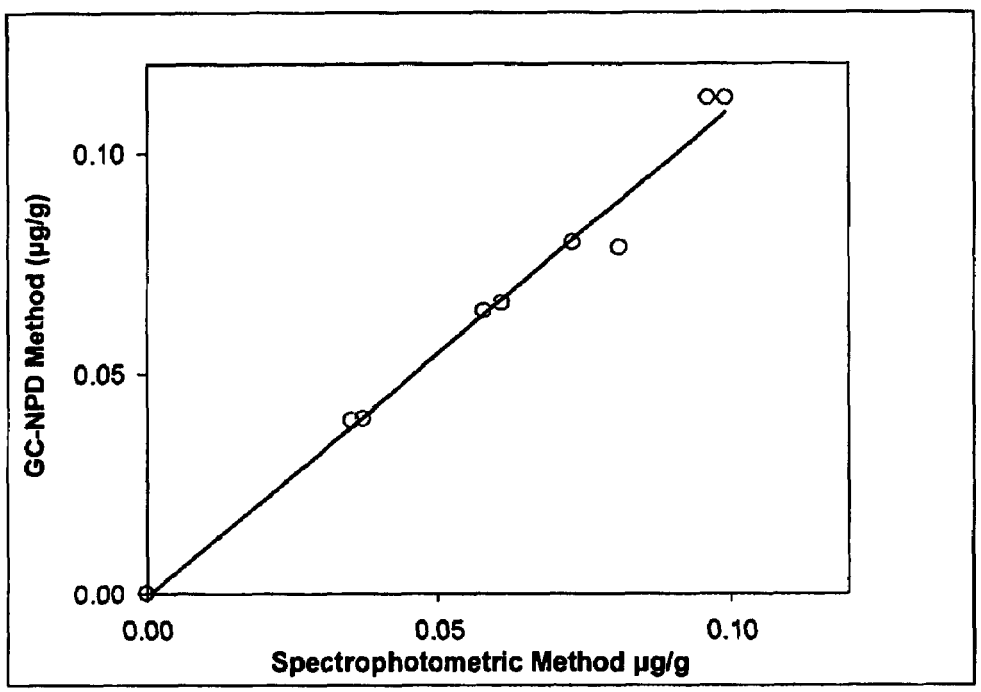
FIG. 4 is a graph showing a correlation between results obtained with the spectrophotometric method and those obtained with the gas-chromatography method.

Since certified wheat (whose exact phosphine level is known) is not available on the market, the accuracy (recovery) of the spectrophotometric method was evaluated by comparing the results obtained with the spectrophotometric method with those obtained with the gas-chromatography method in the analysis of wheat samples contaminated with phosphine. Each sample, therefore, was analysed in parallel by using the two analytic methods. As shown in FIG. 4, a good correlation is obtained, with a value of r=0.9940.

The accuracy was obtained by calculating the standard deviation over three replicates while the accuracy (%) was evaluated by comparing the concentrations obtained by means of the spectrophotometric method with respect to the concentrations obtained by means of GC. The latter are assumed to be the "real" concentrations. The results are summarised in Table 1. The recovery values are in the range of 87-98% with (accuracy) variation coefficients less than 8%.

TABLE 1

Phosphine residue in hard wheat detected with the spectrophotometric method and the GS-NPD method (see text).

| GC-NPD | Spectrophotometry | | |
|---|---|---|---|
| $PH_3 \pm S.D.$ (µg/g) | $PH_3 \pm S.D.$ (µg/g) | RSD (%) | Recovery (%) |
| n.d.[a] | n.d.[b] | — | — |
| 0.040 ± 0.001 | 0.036 ± 0.001 | 5.57 | 91.1 |
| 0.065 ± 0.001 | 0.060 ± 0.002 | 3.38 | 91.4 |
| 0.079 ± 0.001 | 0.077 ± 0.006 | 7.28 | 98.2 |
| 0.112 ± 0.001 | 0.098 ± 0.002 | 2.89 | 87.1 |

[a] not detected (less than the detectable limit, LOD = 0.009 µg/g).
[b] not detected (less than the detectable limit, LOD = 0.026 µg/g).

The above reported experimental data confirm the accuracy and the precision of the spectrophotometric method according to the invention, which is therefore particularly advantageous in order to obtain reliable detections of the total phosphine levels in the cereals in significantly reduced times with respect to the time required by the methods available up to now (about 40 minutes for the method reported by Nowicki T. W. and about 1 hour for the method reported by Rangaswamy J. R.).

The invention claimed is:

1. A method for the detection of phosphine in cereal caryopses, comprising the steps of:
   a) inserting a sample of said cereal caryopses inside a container equipped with hermetic closure;
   b) adding to said sample an aqueous solution of $H_2SO_4$ with a v/v concentration in the range of 5-20%, with obtainment of an aqueous dispersion, and hermetically closing said container;
   c) subjecting said aqueous dispersion contained in said container to the action of microwaves for a time not less than 90 seconds and not greater than 3 minutes;
   d) drawing a predetermined volume of gas overlying said aqueous dispersion and detecting the phosphine possibly present in it by means of colorimetric and/or spectrophotometric methods.

2. Method according to claim 1, wherein said predetermined gas volume into contact with a predetermined volume of an aqueous solution of $AgNO_3$ of known molarity, inside a further container with hermetic closure, and after stirring the absorbance at 400 nm of said aqueous solution is spectrophotometrically measured.

3. The method according to claim 1, further comprising bringing said predetermined gas volume is brought into contact with a bringing said predetermined volume of an aqueous solution of $AgNO_3$ of known molarity to form a solution/mixture, inside a further container with hermetic closure stirring said solution/mixture, and performing a visual analysis of the yellow-brown colour developed in the second container following the reaction between phosphine and $AgNO_3$.

4. The method according to claim 1, wherein the detection of phosphine according to step d) is carried out by placing the aforesaid predetermined gas volume in contact with a paper medium soaked in a reagent capable of developing a colouration by reaction with phosphine, chosen from the group comprising $AgNO_3$, $HgCl_2$, mixtures of $AgNO_3$ and $HgCl_2$ and a mixture of dimethyl yellow, cresol red and $HgCl_2$.

5. The method according to claim 1, wherein the concentration of said aqueous solution of sulphuric acid is about 8-12% v/v.

6. The method according to claim 1, wherein said microwaves have a power in the range of 80-200 W, preferably about 100-140 W.

7. The method according to claim 2, wherein the concentration of said aqueous solution of sulphuric acid is about 8-12% v/v and said microwaves have a power in the range of 80-200 W, preferably about 100-140 W.

8. The method according to claim 6, wherein said aqueous dispersion is subjected to the action of said microwaves for a time in the range of 90-150 seconds.

9. The method according to claim 7, wherein said aqueous dispersion is subjected to the action of said microwaves for a time in the range of 90-150 seconds.

10. The method according to claim 2, wherein the molarity of said $AgNO_3$ solution is in the range of $0.1$-$1.8 \times 10^{-4}$ M.

11. Equipment for the execution of the method according to claim 2, comprising:
   a first container intended to contain an aqueous dispersion of a cereal caryopses sample and an aqueous solution of sulphuric acid and equipped with hermetic closure means;
   means for subjecting the aqueous dispersion contained in the first container to the action of microwaves;
   means for transferring a predetermined aliquot of the gaseous phase overlying the aforesaid aqueous dispersion, developed following the application of the microwaves, to a second container containing an aqueous solution of $AgNO_3$, it too equipped with hermetic closure means; and
   means for the detection of the absorbance at 400 nm of the solution contained in the second container.

12. The equipment according to claim 11, wherein said first container consists of a small bottle with a cap equipped with a puncturable polytetrafluoroethylene baffle, said means for transferring the gaseous phase consist of a gas syringe and said second container consists of a glass vial equipped with a polytetrafluoroethylene cap with puncturable baffle.

13. The equipment according to claim 11, wherein said first container consists of a small bottle with a cap equipped with a puncturable polytetrafluoroethylene baffle, said second container consists of a vacuum tube equipped with cap with puncturable polytetrafluoroethylene baffle, said gastight device and said valve composing said transfer means of the gaseous phase.

* * * * *